United States Patent [19]

Beringer et al.

[11] 4,139,589

[45] Feb. 13, 1979

[54] PROCESS FOR THE MANUFACTURE OF A MULTI-ZONE TABLET AND TABLET MANUFACTURED BY THIS PROCESS

[76] Inventors: Monique Beringer, 2, rue Alexandre Lauly, F-68300 Saint Louis, France; Siegfried Woltmann, Hauptstrasse 255, CH-4322 Mumpf, Switzerland

[21] Appl. No.: 845,025

[22] Filed: Oct. 25, 1977

Related U.S. Application Data

[63] Continuation of Ser. No. 659,050, Feb. 18, 1976, abandoned.

[30] Foreign Application Priority Data

Feb. 26, 1975 [LU] Luxembourg .......................... 71919
Feb. 2, 1976 [LU] Luxembourg .......................... 74291

[51] Int. Cl.[2] .......................... A61K 9/24; A61K 9/68

[52] U.S. Cl. .................................... 264/250; 264/131; 264/134; 424/14; 424/16; 424/21; 424/48; 426/5; 427/3; 427/212; 427/220; 427/299

[58] Field of Search ...................... 424/14, 16, 19–22, 424/48; 426/5; 427/3, 212, 220, 299; 264/131, 134, 250

[56] References Cited

U.S. PATENT DOCUMENTS

| | | | |
|---|---|---|---|
| 462,990 | 11/1891 | Oppenheimer | 424/21 |
| 1,193,423 | 8/1916 | Pryor | 426/5 |
| 1,267,320 | 5/1918 | Fries | 426/5 |
| 1,771,981 | 7/1930 | Mustin | 426/5 |
| 1,771,982 | 7/1930 | Mustin | 426/5 |
| 2,262,087 | 11/1941 | Bartlett et al. | 424/16 |
| 2,536,168 | 1/1951 | Goggin | 424/48 |
| 2,953,497 | 9/1960 | Press | 424/35 |
| 3,048,526 | 8/1962 | Boswell | 424/21 |
| 3,096,248 | 7/1963 | Rudski | 424/35 X |
| 3,922,338 | 11/1975 | Estevenel et al. | 424/21 |

*Primary Examiner*—Shep K. Rose
*Attorney, Agent, or Firm*—Peter K. Kontler

[57] ABSTRACT

Multi-zone pharmaceutical tablets are produced by compressing the contents of a tablet mold. The contents include a granular chewing gum mass and a non-plastic tablet mass, or a chewing gum insert in the recess of a multi-layer non-plastic tablet mass. At least one zone of the tablet, preferably the chewing gum mass, contains a pharmaceutically active ingredient.

3 Claims, 14 Drawing Figures

A B C D E F
VA
VB
VIA
VIB

PROCESS FOR THE MANUFACTURE OF A MULTI-ZONE TABLET AND TABLET MANUFACTURED BY THIS PROCESS

This is a continuation of application Ser. No. 659,050, filed Feb. 18, 1976, now abandoned.

The invention relates to a process for the manufacture of a multi-zone tablet, and to a tablet manufactured by this process.

The zones can be irregularly formed, but can also be regularly formed, for example as layers. In this way a multi-layered tablet is formed.

Multilayered tablets serve, among other things, to keep different active ingredients separate from each other in one and the same preparation by accommodating them in different layers and then administer them together in a predetermined ratio of doses. In many cases, one or more of the active ingredients are required to have a retarded action. An object of the present invention is to provide a process and a tablet of the kind defined above such that with the least possible production costs a tablet is obtained whose active ingredients having a retarded action can be administered orally together with active ingredients having an instant action in human medicine.

The process of the invention is characterized in that a non-plastic tablet mass and a plastic chewing gum mass, whereby one of the said masses contains at least one pharmaceutically active ingredient, are introduced into a tablet mould and with a fitting force plug are compressed to form a joint tablet, having at least one hard zone comprising the tablet mass and at least one plastic zone comprising the chewing gum mass.

The chewing gum mass contains a water-stable portion which, although it can be kneaded in the mouth, cannot be dissolved and cannot be chewed.

The pharmaceutical active ingredients to be administered with an immediate action are mixed with the tablet mass and are very rapidly liberated in the mouth if the hard layer comprising this tablet mass is bitten and/or sucked, whereby it is dissolved. The pharmaceutical active ingredients to be administered with a retarded action are mixed with the plastic chewing gum mass and are released only slowing during the actual chewing. In this way a very uniform supply of the active ingredients over a long period can be obtained. Active ingredients which are difficult or impossible to incorporate homogeneously in a tablet mass due to their oily or otherwise difficult consistency can also be mixed with the plastic mass and moreover can be very uniformly distributed in it. Active ingredients which are too volatile to be satisfactorily incorporated in tablet masses can also be incorporated in the plastic mass since it considerably reduces their volatility.

In addition to or in place of the pharmaceutical active ingredients, flavouring agents or similar substances can be admixed.

It is for this reason that so-called chewing gum and the like, which consist of a core of plastic mass covered with a coating have previously been produced by the process used for producing coating pills. However, the process according to the invention is considerably simpler than the process for coating pills, because it can be performed in conventional pelletizing machines for multilayered tablets, whereby it is merely necessary for the feed and press tools for the tablet mass of one or more tablet layers to be replaced by corresponding tools for processing portions of plastic chewing gum mass.

The tablet mass is generally present in powder or granulate form and the conventional pelletizing machines are designed for the processing thereof. It is therefore recommended to proceed correspondingly when producing the plastic layer and this is preferably carried out by hardening the chewing gum mass by cooling so that it becomes granulatable and is then granulated, whereby as a granulate it is pressed to the plastic portion of the tablet.

In certain circumstances the granulated, greatly cooled chewing gum mass is not pelletizable and it is then recommended to make the said mass pelletizable by heating, whereby when heated it is kept flowable by mixing with non-toxic lubricant powder. It is then introduced into the tablet mould as a pelletizable, flowable, granulated chewing gum mass and pressed.

The plastic and non-plastic mass can be joined together in various ways. A preferred process which is particularly simple to perform, comprises mixing the chewing gum granulate with flowable, non plastic tablet mass, followed by pelletizing. The individual granulate particles then form the zones or several granulate particles of the same mass, which are contiguous with one another, form a common zone.

Another possibility of combining the different masses comprises the pelletization of the individually coated tablet mass and chewing gum mass.

A further possibility of joining the two masses comprises punching the chewing gum mass as a disc from a preformed strip and pressing with the tablet mass to a tablet.

A preformed strip of plastic mass can be easily obtained by rolling. No difficulties are encountered in punching out the disc from such a strip.

The special adhesiveness of the plastic mass and its ability to seal off one substance from another are in many cases advantageous, particularly if two layers of tablets are required to be sealed off from each other or if it is required to increase the resistance of the tablet to breakage. In such a case, the element of plastic mass is inserted as a middle layer. It then seals the two adjacent layers of tablet mass from each other and functions as elastic supporting layer to increase the resistance of the whole tablet to breakage.

Such a sealing layer also enables two chemically incompatible pharmaceutical compositions to be accommodated in one and the same tablet. In that case, one layer of the tablet mass is mixed with the first pharmaceutical composition and the second layer with the second composition so that these chemically incompatible substances are separated from each other by the middle layer. One and the same multilayered tablet may also contain a plurality of interlayered or overlayered plastic elements.

Two chemically incompatible pharmaceutical active ingredients can also be sealed relative to one another by mixing one of the active ingredients into the plastic chewing gum mass and the other into the non-plastic tablet mass.

A further possibility of joining the two masses is brought about by placing the chewing gum mass as a preformed element in a recess of a hard zone pressed from the tablet mass, the recess covering the underside and at least part of the periphery of the said preformed element. Joint pressing to a tablet then takes place.

BRIEF DESCRIPTION OF THE DRAWINGS

Other and further objects of the present invention will be apparent from the following description and claims, and are illustrated in the accompanying drawings which by way of illustration show preferred embodiments of the present invention and the principles thereof, and what are now considered to be the best modes contemplated for applying these principles. Other embodiments of the invention embodying the same or equivalent principles may be used and structural changes may be made if desired by those skilled in the art without departing from the invention and the scope of the appended claims.

In the drawings.

DESCRIPTION OF THE PREFERRED EMBODIMENTS

Figures 1, 2, 3, 4, 5A, 5B, 6A, 6B, 7, 8, 12:
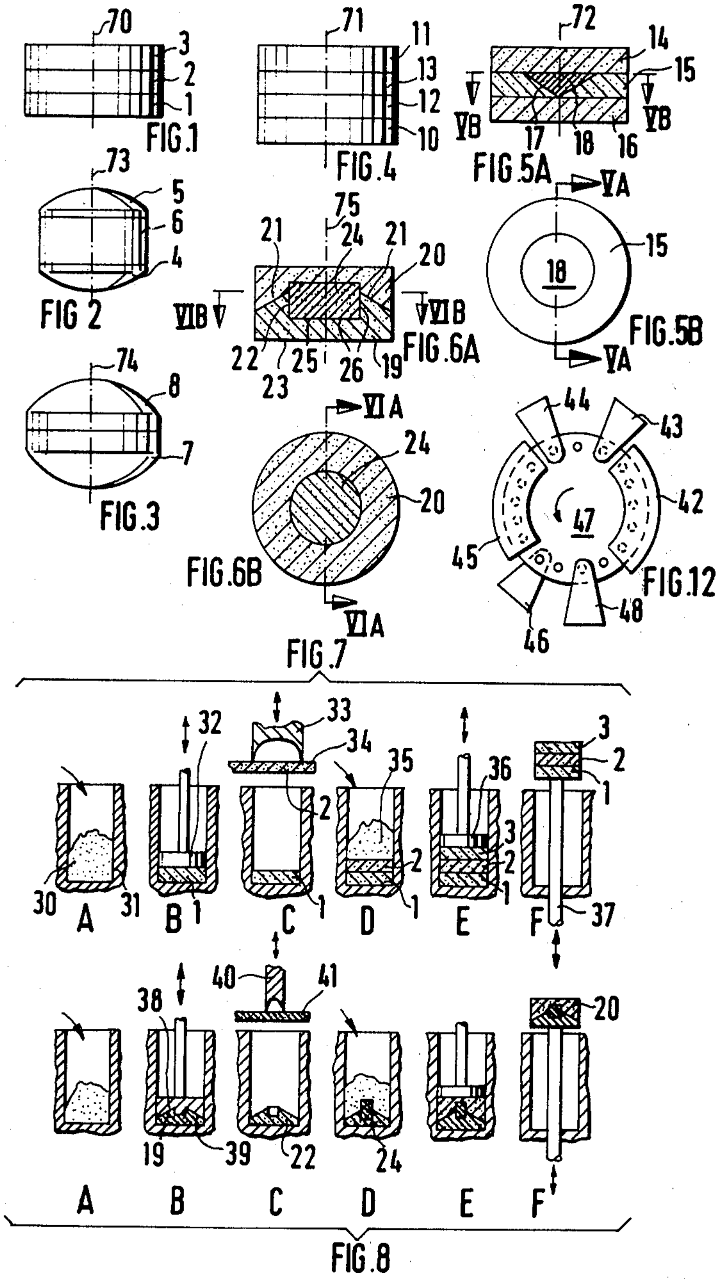
FIG. 1 is a side view of a multilayered tablet.
FIG. 2 is a side view of a multilayered tablet having a biconvex external contour.
FIG. 3 shows by way of example another embodiment of a multilayered tablet having a biconvex external contour.
FIG. 4 is a side view of a four-layered tablet, FIG. 5 (composed of FIGS. 5A and 5B) is a section through a three-layered tablet having a completely embedded preformed element of plastic mass, the FIG. 5A showing the tablet in longitudinal section and the FIG. 5B in cross section, FIG. 6 (composed of FIGS. 6A and 6B) shows another embodiment of a multilayered tablet having a completely embedded preformed element of plastic mass, the FIG. 6A showing the tablet in longitudinal section and the FIG. 6B in cross section.
FIG. 7 illustrates the manufacture of a multilayered tablet according to FIG. 1, using a preformed disc of plastic mass.
FIG. 8 illustrates the manufacture of a multilayered tablet according to FIG. 6.
FIG. 12 is a top plan view of the press drum of a multilayered pelletizing press for carrying out the process according to the invention, comprising an interlayering device for interlayering preformed elements of plastic mass.

In FIG. 1, the reference numeral 1 indicates a first layer pressed from a non-plastic tablet mass, 2 indicates a layer consisting of a preformed disc of plastic mass and 3 indicates a second layer pressed from non-plastic tablet mass. Mixed in with the tablet mass of layer 1 is a pharmaceutical composition which is incompatible with the pharmaceutical composition in layer 3 because it would decompose on contact with it. Layer 2 which extends over the entire cross-section of the tablet here serves also as a separating layer and prevents contact between the two pharmaceutical compositions and hence their decomposition. In FIG. 2, the two layers 4 and 5 consist of tablet mass and layer 6 of plastic mass. In FIG. 3, the two layers 7 and 8 consist of tablet mass and layer 9 of plastic mass. In FIG. 4, layers 10 and 11 consist of tablet mass and layers 12 and 13 of differing plastic masses. The tablet shown in FIG. 4 can be manufactured by first producing the tablet half consisting of layers 11 and 13 and then, independently thereof, the tablet half consisting of layers 10 and 12. Both tablets halves can be produced on the same machine since both consist of a layer of tablet mass and a layer of plastic mass. The multilayered tablet shown in FIG. 4 is then obtained by joining the two halves together. The various layers of tablet mass and various elements or layers of plastic mass of one and the same tablet may have different substances mixed in with them and/or be differently coloured. The tablets shown in FIGS. 1 to 4 are rotationally symmetrical in each case about the dash-dot axis indicated in the Figure, in other words they are circular in cross-section.

In the tablet shown in FIG. 5, the three layers 14, 15 and 16 consist of differing tablet masses. The middle layer 15 is formed to have a conical concentric recess 17 in which a conical preformed element 18 of plastic mass was inserted before layer 14 was pressed on it. The element 18 was placed into the recess 17 as a ball of plastic mass and pressed into the conical form illustrated in the drawing by the tablet mass of the upper layer 14 as this layer was pressed into position.

In the tablet shown in FIG. 6, the two layers 19 and 20 consist of differing tablet masses. Layer 19, which is the lowermost layer, is the first to be formed. It is provided with a conical surface 21 and a central recess 22 which does not extend right down to the bottom 23. A preformed element 24 of plastic mass is fitted into this recess 22 before layer 20 is pressed on it, the undersurface 25 of the preformed element and part of its circumference 26 being thereby covered by the layer 19 while part of it protrudes from the recess 22. Layer 20 of sufficient thickness is then pressed on the surface so that element 24 is completely enclosed inside the tablet mass. The two tablets shown in FIGS. 5 and 6 are also axially symmetrical cylinders but the form of the tablets illustrated may be modified, for example they may be given a polygonal cross-section.

The multilayered tablets according to FIGS. 1 to 6 are axially symmetrical to the particular axis of symmetry 70 to 75, being coated in the direction of the relevant axis of symmetry.

The manufacture of a tablet according to FIG. 1 is illustrated in FIG. 7 where FIG. 7A shows how the tablet mass 30 is dosed in such a quantity that it is just sufficient for layer 1 to fill the die matrix 31 of the press. FIG. 7B shows how in the next step the tablet mass is compressed by a force plug 32 to form the layer 1. When this has been done, a disc 2 cut out of a strip 34 of adhesive plastic mass by means of a punch 33 is placed on layer 1. The disc 2 is punched out to have the same circular cross-section as the opening of the die matrix 31, allowing for the necessary tolerances. In the next step shown in FIG. 7D, a quantity of tablet mass 35 just sufficient for producing layers 3 is poured over layer 1 and 2 which are now placed above one another, and the mass 35 is then compressed by a force plug or ram 36 to form layer 3 as shown in FIG. 7E, and at the same time layers 1, 2 and 3 are bonded together by the pressure applied. The bond between layers 1 and 3 on the one hand and layer 2 on the other is promoted by the adhesiveness of the plastic mass. This enables substantially lower pressures to be applied for pressing with the force plug 36 than would be necessary for bonding together three layers pressed from powder. The pressure applied by the plug 35 should be adjusted so that it is just sufficient to impart the necessary firmness without spreading out the layer 2. The dimensional stability of the preformed layer of plastic mass must be adjusted to the necessary pressure so that the layer will not be forced out of shape. The finished multilayered tablet is then expelled by an ejector stamp 37 as shown in FIG. 7F.

The method of manufacturing the multilayered tablet shown in FIG. 6 is substantially the same as that described with reference to FIG. 7 and the various operational steps illustrated in FIG. 8 correspond to those illustrated above them in FIG. 7. The main difference between the two manufacturing processes is that in the press die 38 which corresponds to the press die 32, the contour of the end face 39 conforms to the desired surface 21 of the layer 19 and that the punch 40 corresponding to the punch 33 cuts a smaller element out of the strip 41 of plastic mass to fit into the recess 22.

Figure 9:
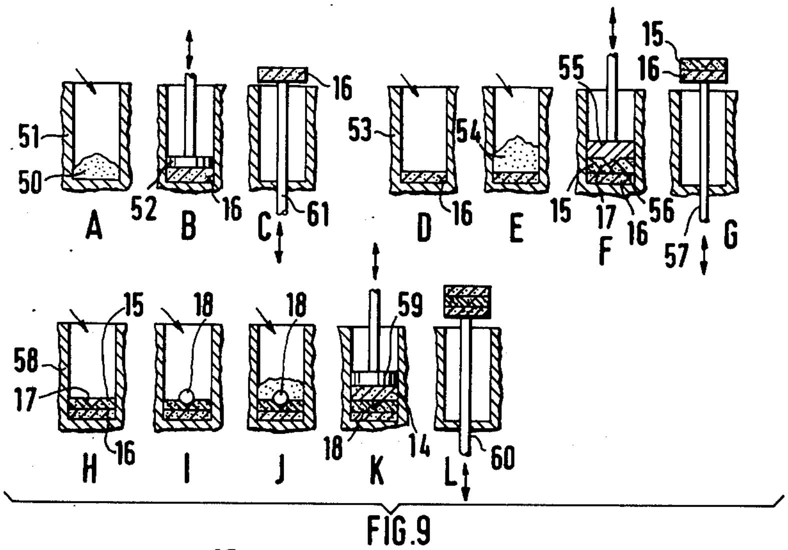
FIG. 9 illustrates the manufacture of a multilayered tablet according to FIG. 5.

According to FIG. 9 illustrating the manufacture of a tablet shown in FIG. 5, the tablet mass 50 is introduced into the matrix 51 in a measured quantity just sufficient to form layer 16. In the next step of the process illustrated in FIG. 9B, the tablet mass is compressed by a force plug 52 to form layer 16, and in the next following step layer 16 is ejected by an ejector stamp 61. Layer 16 has thus been produced in the same way as a single layered tablet and may therefore be produced in a conventional pelletizing machine in exactly the same way as single layered tablets. Layer 16 is then transferred to a second pelletizing machine where it is introduced into the die matrix 53. A measured quantity of tablet mass 54 is then poured on it, (FIG. 9E) and pressed into the form of layer 15 with conical recess 17, using a force plug 55 having a central conical projection 56. In the next step of the process (FIG. 9G) the resulting two layered tablet consisting of layers 16 and 15 is ejected by the ejector stamp 57. The steps of the process illustrated in FIGS. 9D to 9G may be carried out in a conventional pelletizing machine for single layered tablets provided only that it is equipped with an additional feed mechanism and suitable adjustment of the operating cycle for feeding layer 16 according to FIG. 9D.

The two layered tablet composed of layers 15 and 16 is then introduced into the die matrix 58 of a third pelletizing machine with the conical recess 17 facing upwards. In the next phase of the cycle, element 18 is placed in this recess. The element 18 is spherical at this stage and for ease of handling it is covered with a layer of gelatine not shown in the drawing. The element 18 in recess 17 has exactly the same total volume as recess 17. In the next stage of the process, a measured quantity of tablet mass for layer 14 is introduced, and in the next following step (FIG. 9K) this mass is compressed to form layer 14, using a force plug 59 with smooth end face. Since element 18 is of a kneadable consistency and easily deformed, it is pressed by this operation into the recess 17 so that it now completely fills the recess, as shown in FIG. 9K and in FIG. 5. When this step of the process has been completed, the now finished multilayered tablet is removed from the machine by an ejector stamp 60 as shown in FIG. 9L. Steps H to L may also be carried out in a conventional pelletizing machine for single layered tablets if two additional feed mechanisms, namely one for the two-layered tablet composed of layers 15 and 16 as shown in FIG. 9H and one for supplying the element 18 shown in FIG. 1 are arranged in the front of the feed mechanism for the tablet mass according to FIG. 9J. The pressing process illustrated in FIGS. 7B, 8B, 9B and 9F is carried out at sufficiently high intensity to produce layers with sufficient hardness for further treatment. The press operation illustrated in FIGS. 7E, 8E and 9K, in other words the last press operation, is carried out at a higher intensity so that the total tablet will be strong enough for use.

Elements 24, 2, 6, 9 and 13 which also consist of plastic mass may also be covered with non-sticky or sealing material such as gelatine in the same way as element 18 before they are embedded in the substance of the tablet. Gelatine seals the ethereal oils of chewing gum from the remaining tablet substance in the finished tablet and facilitates mechanical handling of the element of plastic mass before it is inserted in the tablet substance.

Before the elements of plastic mass are inserted in the tablet, they are easiest to handle mechanically if they are round, for example if they are spherical or ellipsoidal, and the round form shown in FIG. 9 is therefore preferably used as the starting form for the elements of plastic mass.

The tablets may also be manufactured in two successive pelletizing machines according to FIGS. 7 and 8 in the same way as described with reference to FIG. 9. In this case, steps A and B are carried out in the first pelletizing machine and steps C to F in the following pelletizing machine. Alternatively, a pelletizing machine may be equipped to carry out all steps of the process illustrated in FIGS. 7 to 9. FIG. 12 shows such a machine equipped for the stages shown in FIGS. 7 and 8.

Figure 10:
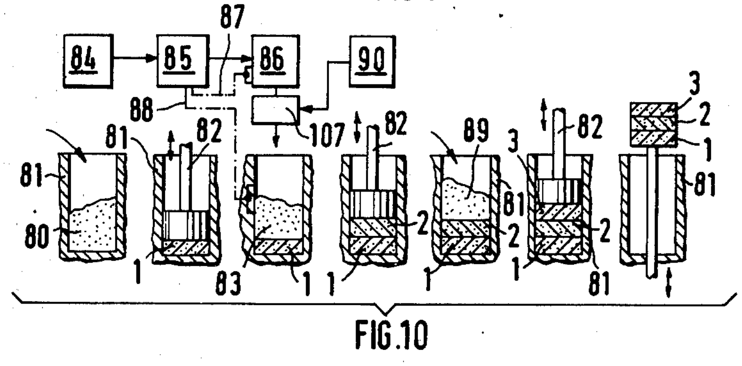
FIG. 10 illustrates the manufacture of a multilayered tablet according to FIG. 1 using a granulated plastic mass.

According to FIG. 10 for manufacturing a multilayered tablet according to FIG. 1 sufficient quantity of tablet mass 80 for the layer 1 is introduced into mould 81 (FIG. 10A) and then compressed with punch die 82 to form layer 1 (FIG. 10B). Sufficient granulated plastic mass 83 is then introduced to form layer 2. This granulated plastic mass is then mixed in a mixer 84, from where it passes to a cooling device 85 where, in a continuous process, it is cooled to a temperature at which the plastic mass is no longer plastic, but is instead breakable and therefore granulated. This cooled plastic mass passes into the grinding apparatus 86 where it is granulated. As indicated by dotted line 87 the grinding apparatus 86 is cooled by the cooling device. In the same way and as indicated by dotted line 88 mould 81 can be cooled.

From grinding apparatus 86 the mass passes into a heatable mixing apparatus 107 and from there the now pelletizable plastic mass passes in the form of a flowable granulate into mould 81 (FIG. 10C) where it is compressed to form layer 2, being simultaneously connected with layer 1 by pressing (FIG. 10D). Then tablet mass 89 for layer 3 is introduced (FIG. 10E) and compressed to give layer 3 (FIG. 10F) and is simultaneously bonded to layer 2. Finally the finished three-layered tablet of FIG. 10G is discharged.

For granulation purposes the chewing gum mass is cooled until it is granulatable. The appropriate temperature for granulation varies from one chewing gum mass to the next, but is in the range −20 to +10° C.

The granulate of the plastic chewing gum mass is heated to about 18° C. in the heatable mixing apparatus 107 to make it easily pelletizable. If the chewing gum granulate is cooler it cannot be pelletized so well. Under certain circumstances, however, the chewing gum granulate at 18° C. is sticky and consequently not sufficiently flowable, hence it is coated with a lubricant. Suitable lubricants are e.g. pulverized stearic acid, pulverized hardened castor oil, pulverized polyglycol, pulverized tallow, pulverized paraffin wax whose melting point is 50 to 52° C., pulverized metal soaps such as magnesium stearate or a mixture of several of these substances. An adding device 90 according to FIG. 10 is used for adding these lubricants and passes a metered portion of lubricant into mixing apparatus 107 where it is mixed with the granulate.

Figure 11:
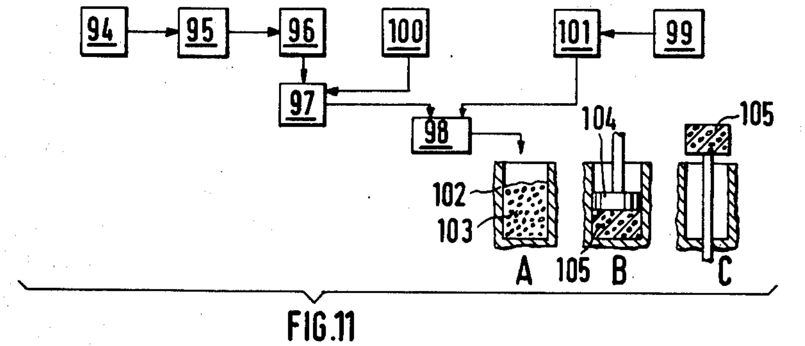
FIG. 11 shows the production of a multilayered tablet from a granulate mixture.

According to FIG. 11 plastic chewing gum mass is mixed in a mixer 94, from where it passes to a cooling device 95 where it is cooled in a continuous process to −10° C. The cooled and consequently no longer plastic mass, which has become breakable and therefore granulatable, is passed into grinding apparatus 96, where it is granulated. The granulate passes into the heated mixing apparatus 97 where it is heated to 18° C. and mixed with lubricants from adding device 100. On leaving mixer 97 the chewing gum granulate is flowable and pelletizable and passes into a mixer 98. Reference numeral 99 designates a store for non-plastic tablet mass in block form, granulated in grinding apparatus 101. The tablet mass granulate from grinding apparatus 101 also passes into mixer 98. The two granulates are mixed in mixer 98 and pass portionwise into mould 102. Punch die 104 presses each portion of granulate 103 into a multi zone tablet 105 (FIG. 11B), which is then discharged according to FIG. 11C.

FIG. 12 shows a top plan view of a press drum 47 having a total of 17 cylindrical press matrices corresponding to matrix 31 uniformly distributed over its circumference. The drum rotates stepwise at intervals from one matrix to the next in the direction of the arrow so that the matrices successively enter into the range of action of different tools. They first come under the action of a filling tool 48 by which they are filled with material according to FIG. 7A or 8A, then under the action of the press tool 42 for pressing according to FIG. 7B or 8B, then under the action of a punching tool 43 which contains a reserve of strips of plastic mass for carrying out the interlayering operation according to FIG. 7C or 8C, then under the action of a feed tool 44 for supplying the tablet mass according to FIG. 7D or 8D, then under the action of a press tool 45 for carrying out the pressing operation according to FIG. 7E or 8E and finally under the action of an ejector tool 46 for ejection according to FIG. 7F or 8F.

The multilayered tablets shown in FIGS. 1 to 6 may in addition be provided with a covering (not shown).

Some examples illustrating the chemical composition of multilayered tablets according to the invention will now be given. In all these examples the pressure exerted during tablet manufacture is 1000kg/cm$^2$ and the finished tablet weight is 1.5g. In the three-layered tablets of the following examples each layer weighs 0.5g.

EXAMPLE 1

In a three-layered tablet according to FIG. 1 the middle layer 2 of plastic contains the following constituents:

1.75 parts by weight of chicle gum,
0.5 parts by weight of paraffin wax,
0.06 parts by weight of tolu balsam,
0.03 parts by weight of Peru balsam,
0.03 parts by weight of alum;

the outer hard layer 1 of the tablet mass contains:

99.0 parts by weight of grape sugar and
1.0 part by weight of the active ingredient quinine;

and the other outer hard layer 3 of the tablet mass contains:

98.0 parts by weight of grape sugar and
2.0 parts by weight of the flavouring agent caramel.

This multilayered tablet is an anti-smoking tablet in which the plastic layer can be chewed as chewing gum long after the tablet has been taken in by the mouth while the alum in the tablet stimulates the flow of saliva which, as has been found by experience, reduces the craving for smoking.

EXAMPLE 2

In a three-layered tablet according to FIG. 1 the middle layer 2 of plastic mass contains the following constituents:

1.70 parts by weight of chicle gum,
0.5 parts by weight of sugar
0.5 parts by weight of paraffin wax,
0.06 parts by weight of tolu balsam,
0.03 parts by weight of inpecacuanha,
0.03 parts by weight of eucalyptus;

one outer hard layer 1 of the tablet mass contains:

50.0 parts by weight of grape sugar,
48.0 parts by weight of sorbitol and
1.0 part by weight of the active ingredient fennel oil;

and the other outer layer 3 of the tablet mass contains:

50.0 parts by weight of grape sugar,
48.0 parts by weight of sorbitol, 1.0 part by weight of the active ingredient eucalyptus oil and
1.0 part by weight of the active ingredient fennel oil.

This multilayered tablet is an antitussive in which the plastic layer continues to be able to be chewed as chewing gum long after the tablet has been taken in by mouth while the ipecacuanha and eucalyptus, as is well known, reduce coughing.

EXAMPLE 3

Similar to Example 2 but with a plastic mass composed of the following constituents:

1.80 parts by weight of chicle gum,
0.15 parts by weight of sugar,
0.02 parts by weight of paraffin wax,
0.01 parts by weight of tolu balsam,
0.01 parts by weight of ipecacuanha, 0.01 parts by weight of eucalyptus.

EXAMPLE 4

Similar to Example 2 but with a plastic mass composed of the following constituents:

1.00 parts by weight of chicle gum,
0.75 parts by weight of sugar,
0.20 parts by weight of paraffin wax,
0.03 parts by weight of tolu balsam,
0.01 parts by weight of ipecacuanha,
0.01 parts by weight of eucalyptus.

EXAMPLE 5

Similar to Example 2 except that 0.03 parts by weight of narcotine are mixed into the plastic mass instead of 0.03 parts by weight of ipecacuanha and 0.03 parts by weight of eucalyptus. This tablet is again an antitussive. In this case the narcotine incorporated to have a retarded action continues to ease coughing for a long time.

EXAMPLE 6

Plastic mass consisting of:

1.75 parts by weight of chicle gum,
0.48 parts by weight of paraffin wax,
0.06 parts by weight of tolu balsam, 0.03 parts by weight of Peru balsam and p1 0.03 parts by weight of alum;

is cooled to −10° C. and granulated to a granulate size of 1 to 1.5mm. The granulate is kept dry and heated to +18° C. The granulate is then mixed with 0.02 parts by weight of paraffin wax, comminuted to 30–50 microns and coated with solid paraffin wax, which serves as a lubricant. The granulate made flowable by the paraffin wax coating is pelletizable at +18° C. and is introduced into a mould and pelletized with the chewing gum portion of a multi-zone tablet.

EXAMPLES 7 to 11

As in Example 6, but using the plastic chewing gum masses in the compositions according to Examples 2 to 5, whereby in each case 0.02 parts by weight of paraffin wax are used as the lubricant.

EXAMPLE 12

Flowable and pelletizable granulate formed from the plastic chewing gum mass, produced according to Example 6 is mixed in a weight ratio of 1:1 with granulate from the tablet mass. This tablet mass consists of 99 parts by weight of grape sugar and 1 part by weight of quinine. The mixed granulate is pelletized in a pelletizing mould to yield multi-zone tablets.

What is claimed is:

1. A process for the manufacture of an inlaid tablet, comprising the steps of incorporating into a plastic chewing gum mass a sustained-release ingredient selected from the group consisting of anti-smoking alum and antitussives; incorporating into a non-plastic tablet mass a substantially immediate-release pharmaceutically active ingredient selected from the group consisting of quinine, fennel oil and eucalyptus oil; and respectively converting said chewing gum mass and said tablet mass into the core and the outer layer of the inlaid tablet.

2. A process as defined in claim 1, wherein said step of converting said chewing gum mass into said core comprises cooling the chewing gum mass so that the chewing gum mass hardens, and converting the hardened chewing gum mass into granulate.

3. A process as defined in claim 1, wherein said converting step comprises converting said tablet mass into a recessed preformed element, converting the chewing gum mass into said core, inserting said core into the recess of said preformed element, introducing the preformed element and the core into a tablet mold, and subjecting the preformed element and the core in the mold to pressure.

* * * * *